(12) United States Patent
Lin et al.

(10) Patent No.: US 8,031,833 B2
(45) Date of Patent: Oct. 4, 2011

(54) PORTABLE INSPECTION APPARATUS FOR X-RAY TOMOGRAPHY

(75) Inventors: Ta-Te Lin, Taipei (TW); Joe-Air Jiang, Taipei (TW); Wan-Lin Hu, Taipei (TW); Cheng-Shiou Ouyang, Taipei (TW); Man-Miao Yang, Taichung (TW); En-Cheng Yang, Taipei (TW)

(73) Assignee: National Taiwan University, Taipei (TW)

( * ) Notice: Subject to any disclaimer, the term of this patent is extended or adjusted under 35 U.S.C. 154(b) by 87 days.

(21) Appl. No.: 12/628,955

(22) Filed: Dec. 1, 2009

(65) Prior Publication Data

US 2011/0026670 A1    Feb. 3, 2011

(30) Foreign Application Priority Data

Jul. 29, 2009 (TW) ................................ 98125595 A

(51) Int. Cl.
*A61B 6/00* (2006.01)
(52) U.S. Cl. ............................. 378/21; 378/57; 378/208
(58) Field of Classification Search .................... 378/20, 378/57, 208, 21
See application file for complete search history.

(56) References Cited

U.S. PATENT DOCUMENTS

2003/0031293 A1* 2/2003 Aust et al. ....................... 378/57
* cited by examiner

*Primary Examiner* — Courtney Thomas

(57) ABSTRACT

An inspection apparatus for tomographing an object includes a moving unit and a rotating unit, which is disposed on the moving unit and rotates the object to be tomographed. A method for tomographing an object includes steps of disposing an object on an inspection apparatus; rotating the object by operating the inspection apparatus; and tomographing the object.

10 Claims, 2 Drawing Sheets

PORTABLE INSPECTION APPARATUS FOR X-RAY TOMOGRAPHY

FIELD OF THE INVENTION

The present invention relates to the technology of X-ray tomography, especially to a portable inspection apparatus for the X-ray tomography.

BACKGROUND OF THE INVENTION

The research on the nondestructive inspection technologies is quite important for the development of industry and trade. These techniques play important roles in the industrial quality management and in the agricultural pest quarantine. For example, in the agriculture, after entering the World Trade Organization (WTO), several countries need the accurate quarantine for the agricultural products and the associated technologies after adopting the globalization. Although the traditional sampling operated by human and the microscopic anatomy inspections are effective, the human errors often occurred under the pressure of fast custom clearance. Besides, it is hard to distinguish whether the surface damage of the fruits is made by the collision or by the pest, and the long-term experiences are necessary for the correct judgment. However, if the perspective images of the internal parts of the fruits acquired by the nondestructive methods are available as the objective quarantine standards, the impact of the damage of pests on agriculture and ecosystem can be avoidable.

Regarding the nondestructive inspection methods, the most frequently used one is X-ray. Therefore, the X-ray tomography becomes one of the most important technologies for the nondestructive methods. When the internal features of the inspected object are complicated or even overlapped and intervened, the general planar scanning cannot provide sufficient resolutions. The tomography can make up this insufficiency and provide the more detailed information to the users. For the industrial applications, the quality control engineer can clearly indentify the internal structures to improve the yield rate; for the agricultural applications, the quarantine officials can easily observe the detail symptoms or the canals bored by the pests. Therefore, the invasion of the alien pests can be avoided, and the edible security can be improved.

However, not every type of the X-ray machines can perform the tomography. Moreover, there are some problems of the professional computerized tomography machines including the mammoth dimensions, expensiveness and unavailability to some operation places.

Please refer to FIG. 1, which is the schematic diagram showing the computerized tomography machine of the prior art. The tomography machine 1 includes a bed 10 set up on the floor, and the object 2 to be inspected is disposed on the bed 10. In FIG. 1, the object 2 to be inspected is a person. The tomography machine 1 further includes an emitter head 14 and the sensing element 16, both of which are configured on the rotating rack 12b, which in turn is pivotally configured on the stand 12a. Usually, there is a motor inside the stand 12a for rotating the rotating rack 12b, and the stand 12a is set up on the floor by means of the foundation 12. The tomography machine 1 can obtain the absorption curves of the object 2 with 360 degrees through the rotation of the rotating rack 12b. These signals are used for the reconstruction of the crossing section images. Since the images are based on the object 2, the geometric central axis must be aligned to superimpose the rotating axis 100. Accordingly, the emitter head 14 and the sensing element 16 can accurately rotate around the geometric central axis of the object 2, so the object 2 can be exposed within the irradiation area of the X-ray.

It can be seen from FIG. 1 that the mammoth dimensions of the computerized tomography machine 1 majorly results from the bed 10 and the rotating rack 12b, which occupies the most space. Due to the rotation of the rotating rack 12b, no article can be disposed in the space swept by the rotating rack 12b, otherwise the collisions between the article and the emitter head 14 or between the article and the sensing element 16 will occur. Thus, in order to install the tomography machine 1, the accommodated space can not be too small. However, for the production lines of the products or for the packaging lines and the conveyer belts of the fruits and vegetables, the conventional tomography machine 1 is too big. Furthermore, during the tomographing, the object 2 is moving along the rotating axis 100 so as to obtain the images of 360 degrees in different sections of the object 2. For the human body as the object 2, these sections include chest, head, abdomen, etc. However, the moving way of the object 2 is not applicable to the operation of the production lines. Moreover, the location of the object 2 may interfere with the conveyer belt of the production line, and this condition would cause the inaccurate result of the tomography. In addition, since the dimensions of the emitter head 14 and the sensing element 16 are mammoth, the rotating speed thereof is slow, and it is not cost-effective and applicable for the production lines where the efficiency is highly emphasized.

In order to solve the above mentioned problems, the development team of the present invention has done a lot of analyses on the drawbacks of the conventional technologies. Finally the portable inspection apparatus for x-ray tomography is invented and is able to overcome the drawbacks of the conventional technologies.

SUMMARY OF THE INVENTION

The present invention can reach the high accuracy, reduce the operation cost, and greatly raise the tomographing efficiency. The general digital X-ray machines with point light source or parallel light source can be incorporated with the apparatus of the present invention for tomographing. The proposed apparatus is so compact that it can be set up inside the inspection chamber. Therefore, the profile images of the object with high accuracy can be obtained without the influence of the original conveying device. In addition, adapted to the characteristics of the X-ray machine, this apparatus can be easily installed and uninstalled with high usage flexibility and high accuracy by means of the mechanisms as well as the algorithms.

In accordance with one aspect of the present invention, an inspection apparatus for tomographing an object is provided. The inspection apparatus comprises a moving unit; and a rotating unit disposed on the moving unit and rotating the object to be tomographed.

In accordance with another aspect of the present invention, a method for tomographing an object is provided. The method for tomographing an object comprises steps of disposing an object on an inspection apparatus; rotating the object by operating the inspection apparatus; and tomographing the object.

Preferably, the method is an X-ray tomography method.

Preferably, the step of tomographing the object is performed under an X-ray apparatus having an emitting direction, the object is rotated around a rotating axis, and the method further comprises a step of adjusting the rotating axis to be perpendicular to the emitting direction.

Preferably, the method further comprises a step of moving the object by operating the inspection apparatus when tomographing the object.

Preferably, the steps of rotating the object and moving the object are performed in a condition including one selected from a group consisting of simultaneously, sequentially, and alternately.

Preferably, the inspection apparatus comprises a moving unit horizontally moving the object; and a rotating unit disposed on the moving unit and rotating the object, wherein the object is disposed on the rotating unit.

Preferably, the moving unit comprises a first sliding rail; a first moving structure moving along the first sliding rail in a first moving direction; a second sliding rail disposed on the first moving structure; and a second moving structure moving along the second sliding rail in a second direction perpendicular to the first direction, wherein the rotating unit is disposed on the second moving structure.

Preferably, the moving unit further comprises an elevating structure mounted on the first moving structure and elevating the second moving structure. The second sliding rail is mounted on the elevating unit.

In accordance with a further aspect of the present invention, an inspection apparatus for tomographing an object is provided. The inspection apparatus comprises a rotating unit rotating the object to be tomographed.

Preferably, the inspection apparatus further comprises a fixture disposed on the rotating unit and fixing the object onto the rotating unit.

Preferably, the inspection apparatus further comprises a moving unit, wherein the rotating unit is mounted on the moving unit.

Preferably, the moving unit comprises a first sliding rail; a first moving structure moving along the first sliding rail in a first moving direction; a second sliding rail disposed on the first moving structure; and a second moving structure moving along the second sliding rail in a second direction, wherein the rotating unit is disposed on the second moving structure.

Preferably, the first moving direction is perpendicular to the second moving direction, and the rotating unit has a rotating axis parallel to one of the first direction and the second direction.

Preferably, the inspection apparatus further comprises a first screw rod driving the first moving structure; and a second screw rod driving the second moving structure.

Preferably, the inspection apparatus further comprises a first motor powering the first screw rod to drive the first moving structure; and a second motor powering the second screw rod to drive the second moving structure, wherein the first and the second motors are stepping motors.

Preferably, the moving unit further comprises an elevating structure mounted on the first moving structure and elevating the second moving structure, wherein the second sliding rail is mounted on the elevating unit.

Preferably, the object is tomographed under an X-ray apparatus having an emitting direction, wherein the rotating unit has a rotating axis perpendicular to the emitting direction.

The above objects and advantages of the present invention will become more readily apparent to those ordinarily skilled in the art after reviewing the following detailed descriptions and accompanying drawings, in which:

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

Figure 1:
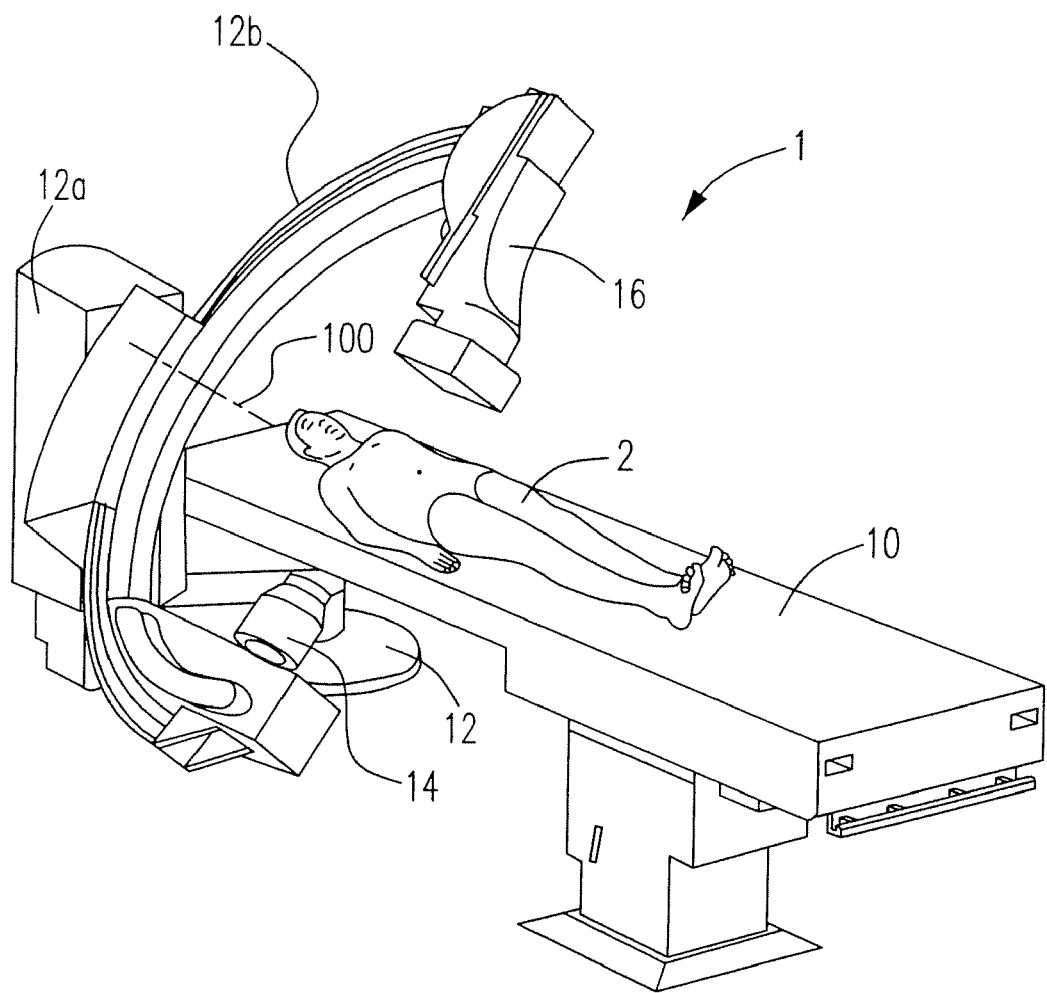
FIG. 1 is the schematic diagram showing the computerized tomography machine of the prior art.
Figure 2:
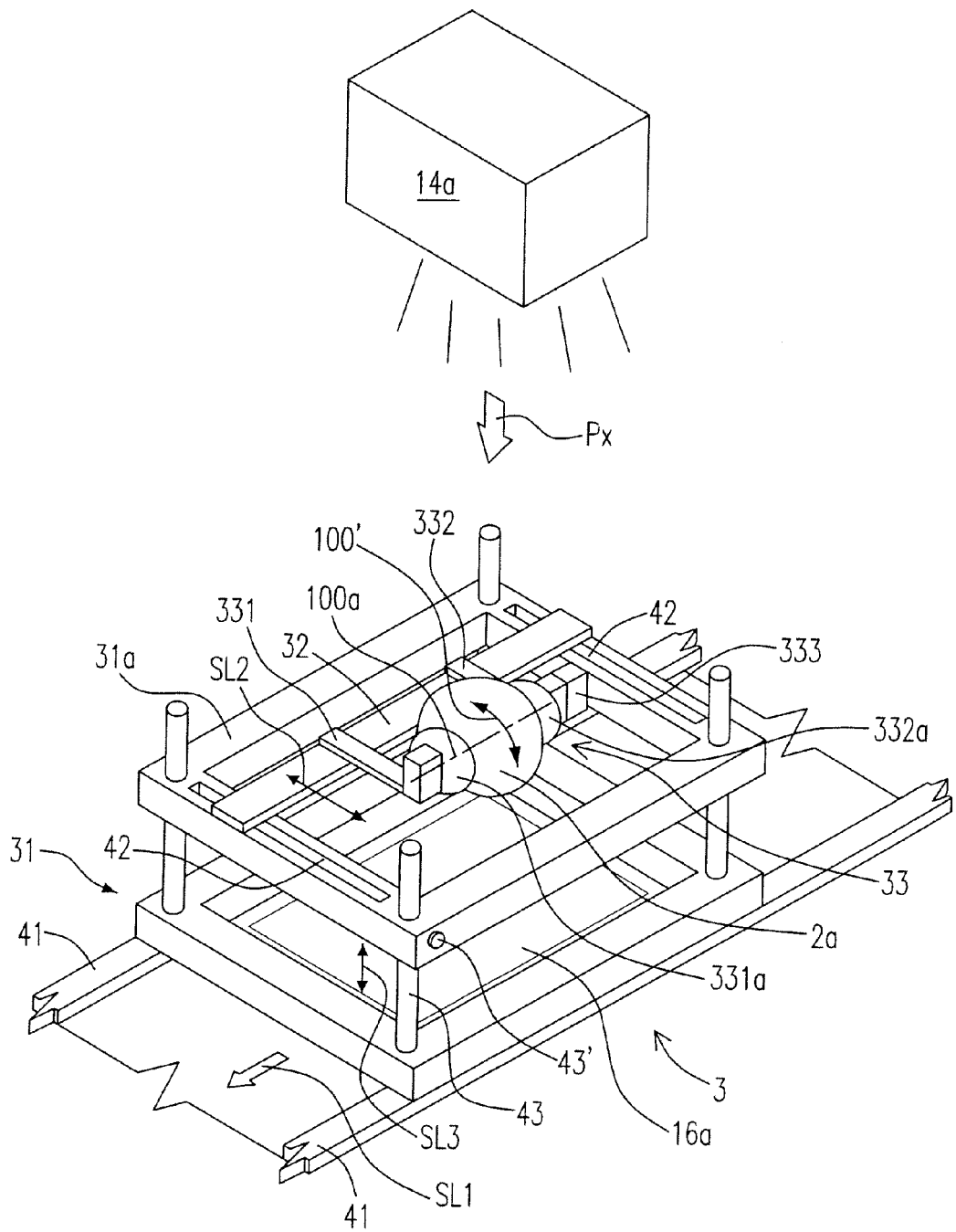
FIG. 2 is the schematic diagram showing the 3-dimensional view of the inspection apparatus of the present invention.

Please refer to FIG. 2, which is the schematic diagram showing the 3-dimensional view of the tomography machine and the portable inspection apparatus. In FIG. 2, the fixture 33 has a rotating axis 100a parallel to the ground. The emitter head 14a of the X-ray machine is usually an emitter head of a digital X-ray machine. The emitting direction Px of the emitter head 14a is perpendicular to the rotating axis 100a. The fixture 33 fixes the object 2a, e.g. a fruit. There is a sensing element 16a below the object 2a to be inspected for receiving the X-ray signal from the emitter head 14a. The object 2a is rotating around the rotating axis 100a. That is, the object 2a is spinning relative to the emitting direction Px, so that the absorption curves of 360 degrees can be obtained to rebuild the images of the cross sections. It can be seen that the relative motion of the object 2a and the emitter head 14a in FIG. 2 of the present invention is the same as that in FIG. 1 of the prior art. However, the difference between the present invention and the prior art is that only the object 2a is rotating to obtain the absorption curves of 360 degrees; while the emitter head 14 and the sensing element 16 are rotating around the object 2 in the prior art as shown in FIG. 1. In another aspect, the emitter head 14a is motionless relative to the ground in the present invention; while the emitter head 14 and the sensing element 16 are in motion relative to the ground in the prior art. If the object 2a shown in FIG. 2 is a fruit, since its dimensions are small, it is easier to rotate the fruit. To imagine, if the object 2a in FIG. 2 is not rotating, while the emitter head 14a is rotating, then the rotating rack 12b as shown in FIG. 1 is required. In such conditions, it can be easily to figure out that the needed space for the apparatus of the present invention is much smaller than that for the prior art.

Please continue to refer to FIG. 2. The fixture 33 further includes a first fixing part 331 and a second fixing part 332, between which the object 2a is fixed. In addition, one of the fixing parts, e.g. the second fixing part 332 in FIG. 2, can be installed with a motor 333, which is usually a stepping motor. The rotating axis of the motor 333 is operated as the rotating axis 100a of the object 2a. In order to rotate the object 2a on the fixture 33 driven by the motor 333, a first fixing element 331a and a second fixing element 332a are pivotally configured on the first and the second fixing parts 331 and 332, respectively. In FIG. 2, the second fixing element 332a is connected with the rotating shaft of the motor 333, and thus the motor 333 can rotate the second fixing element 332a so as to rotate the object 2a. Accordingly, the object 2a can spin around the rotation direction 100' relative to the emitter head 14a so as to obtain the absorption curves of 360 degrees.

Please continue to refer to FIG. 2. The whole construction below the emitter head 14a is the inspection apparatus 3, on which the fixture 33 is disposed. The inspection apparatus 3 further includes a horizontal moving device to allow the horizontally movement of the fixture 33 relative to the emitter head 14a. The horizontal moving device includes a first sliding structure 31 sliding along the first sliding direction SL1 parallel to the rotating axis 100a of the object 2a. Accordingly, when the first sliding structure 31 slides along the first sliding direction SL1, the fixture 33 will move along the same direction, so the X-ray machine can obtain the absorption curves of 360 degrees for the different sections along the rotating axis 100a. In addition, the first sliding structure 31 slides on the first sliding rail 41.

Please continue to refer to FIG. 2. In order to allow the object 2a to be located in the center point of the emitting direction Px of the emitter head 14a, the object 2a can also move along the direction perpendicular to the first sliding direction SL1 in addition to move along the first sliding direction SL1. Therefore, the second sliding structure 32 is disposed on the first sliding structure 31, and can slide along the second sliding direction SL2, which is perpendicular to the first sliding direction SL1 or the rotating axis 100a. In order to allow the fixture 33 to have dual degrees of freedom for moving, the fixture 33 is disposed on the second sliding structure 32, which in turn is disposed on the first sliding structure 31. Accordingly, the fixture 33 has dual degrees of freedom for moving.

Please continue to refer to FIG. 2. In order to adjust the distance between the object 2a and the emitter head 14a, the vertical guiding rods 43 are disposed on the first sliding structure 31, and can be controlled via the knob 43'. The elevating base 31a can be configured through the vertical guiding rods 43, and can move up and down along the vertical guiding rods 43 in the third sliding direction SL3. It can be seen from FIG. 2 that the second sliding structure 32 is disposed on the elevating base 31a so that the object 2a fixed by the fixture 33 can be moved up and down. The second sliding rail 42 can be disposed on the elevating base 31a for the sliding of the second sliding structure 32. Since the first and the second sliding structures have two perpendicular degrees of freedom for moving, the combination of the first and the second sliding structures can be called the horizontal moving device, which makes the object 2a move horizontally corresponding to the location of the emitter head 14a. The whole set of various structures extended from the fixture 33 can be the inspection apparatus of tomography. That is to say, the inspection apparatus at least includes the fixture 33, further includes the first sliding structure 31 with the accompanied first sliding rail 41, and further includes the second sliding structure 32 with the accompanied second sliding rail 42 and the elevating base 31a, etc.

In addition, regarding the movements along the first sliding direction SL1 and the second sliding direction SL2, the stepping motor usually can be used to drive the guide screw, which in turn drives the screw base to move. Since the guide screw is frequently used techniques, it would not be described here in detail.

In the applications of the present invention, the inspection apparatus of the present invention can be easily installed inside the inspection chamber, which is not shown in the figures. When applying the present invention, because only the object 2a is rotating, no large space is needed to accommodate the rotating rack 12b in the prior art as shown in FIG. 1. That is, there is no need to worry the risks of the interferences or even the collisions between the rotating rack 12b and any article in the space occupied by the rotation of the rotating rack 12b. As to the required space for the operation of the present invention, the required length and width are approximately equal to the length and width of the inspection apparatus, and the required height is determined by the location the emitter head 14a.

Besides, the automatic continuous cross section tomography can be done in the present invention according to the user's setting to further reduce the time the operators stay in the radiation-control area. From the technical view, the key factors to affect the quality of the rebuilt images are whether the rotating axis is located at the center of the line sensor and whether the aberration on the edge caused by the point light source is properly corrected. Therefore, in order to eliminate the deviation for the location of the rotating axis when the tomography system is set up, the data can be automatically corrected for the deviation in the present invention, and the aberration on the edge can be corrected based on the distances between the light source and object and between the light source and the sensor. The noise filtration algorithm can be introduced during the calculation, and finally the image quality can be ensured. Moreover, by applying the software system accompanied in the present invention, the users can set the data quantity for rebuilding cross section images to satisfy the requirements for the image quality and the scanning speed under various conditions.

Furthermore, for those users who have already had digital X-ray machines, the present invention can contribute the great benefits for them. The users only need to dispose the inspection apparatus of the present invention between the emitter head and the sensing element of the X-ray machine, and then the object can be tomographed accordingly. Since the inspection apparatus is independent from the original conveyance device, the accuracy will not be deteriorated by the influence the conveyance device. Besides, the inspection apparatus can be installed in general planar digital X-ray machines. That is, the inspection apparatus can be applied to those X-ray machines, and the inspection apparatus itself does not include the X-ray machine. In such conditions, the dimensions of the inspection apparatus of the present invention is much smaller than those of the X-ray tomography machine in the prior art, and the weight of the inspection apparatus of the present invention is much lighter as well. Therefore, the inspection apparatus of the present invention is a portable inspection apparatus. For those users, who have planer digital X-ray machines, not X-ray tomography machines, but want to do the tomography, the service provider can easily carry the inspection apparatus of the present invention to the users for providing the services of the tomography for the objects To sum up, the present invention provides an inspection apparatus for the X-ray tomography, and can be applied to general digital X-ray machines. The highly accurate positioning mechanism, i.e. the inspection apparatus, with four degrees of freedom in two horizontal moving directions, one vertical moving direction, and one rotating direction for the object is developed in the present invention. In addition, the positions for the second sliding direction and the third sliding direction, i.e. elevating direction, can be adjusted according to the size of the object and the magnification factor, respectively. The stepping motor can rotate the object 2a to obtain the sinogram, constituted by scanning in the different angles in the same cross section. The appropriate parameters and algorithms can be selected for processing the sinogram images for building the images of the cross section. For obtaining the images of the cross sections in the different positions on the object 2a, the first sliding direction SL1 is parallel to the rotating axis 100a of the object 2a, and the stepping motor can drive a screw rod to move the first sliding structure 31 along the first sliding rail 41. Then the object 2a can move in the first sliding direction SL1, which is perpendicular to the radiation direction of the X-ray machine for obtaining the images of the cross sections in the different positions on the object 2a.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An inspection apparatus for tomographing an object, comprising:
   a moving unit including:
      a first sliding rail;
      a first moving structure moving along the first sliding rail in a first moving direction;
      a second sliding rail disposed on the first moving structure; and
      a second moving structure moving along the second sliding rail in a second direction; and
   a rotating unit disposed on the second moving structure and rotating the object to be tomographed, wherein the object to be tomographed is disposed on the rotating unit.

2. An inspection apparatus according to claim 1, wherein the moving unit further comprises an elevating structure mounted on the first moving structure and elevating the second moving structure, and the second sliding rail is mounted on the elevating unit.

3. An inspection apparatus for tomographing an object, comprising:
   a rotating unit rotating the object to be tomographed; and
   a moving unit, including:
      a first sliding rail;
      a first moving structure moving along the first sliding rail in a first moving direction;
      a second sliding rail disposed on the first moving structure; and
      a second moving structure moving along the second sliding rail in a second direction, wherein the rotating unit is disposed on the second moving structure.

4. An inspection apparatus according to claim 3, further comprising a fixture disposed on the rotating unit and fixing the object onto the rotating unit.

5. An inspection apparatus according to claim 3, wherein the rotating unit is mounted on the moving unit.

6. An inspection apparatus according to claim 3, wherein the first moving direction is perpendicular to the second moving direction, and the rotating unit has a rotating axis parallel to one of the first direction and the second direction.

7. An inspection apparatus according to claim 3, further comprising:
   a first screw rod driving the first moving structure; and
   a second screw rod driving the second moving structure.

8. An inspection apparatus according to claim 7, further comprising
   a first motor powering the first screw rod to drive the first moving structure, wherein the motor is a stepping motor.

9. An inspection apparatus according to claim 3, wherein the moving unit further comprises an elevating structure mounted on the first moving structure and elevating the second moving structure, wherein the second sliding rail is mounted on the elevating unit.

10. An inspection apparatus according to claim 3, wherein the object is tomographed under an X-ray apparatus having an emitting direction, wherein the rotating unit has a rotating axis perpendicular to the emitting direction.

* * * * *